(12) United States Patent  
Dworschak et al.

(10) Patent No.: US 7,393,348 B2  
(45) Date of Patent: Jul. 1, 2008

(54) TWO-PART MEDICAL INSTRUMENT

(75) Inventors: Manfred Dworschak, Duerbheim (DE); Theodor Lutze, Balgheim (DE); Pedro Morales, Tuttlingen-Nendingen (DE); Dieter Weisshaupt, Immendingen (DE)

(73) Assignee: AESCULAP AG & Co. KG, Tuttlingen (DE)

( * ) Notice: Subject to any disclaimer, the term of this patent is extended or adjusted under 35 U.S.C. 154(b) by 0 days.

(21) Appl. No.: 11/065,525

(22) Filed: Feb. 23, 2005

(65) Prior Publication Data

US 2005/0154377 A1     Jul. 14, 2005

Related U.S. Application Data

(63) Continuation of application No. PCT/EP2003/009433, filed on Aug. 26, 2003.

(30) Foreign Application Priority Data

Sep. 5, 2002   (DE) .............................. 102 42 152

(51) Int. Cl.
    *A61B 17/00*   (2006.01)
(52) U.S. Cl. .......................................... 606/1; 606/208

(58) Field of Classification Search .................... 606/1, 606/51, 52, 205–208
See application file for complete search history.

(56) References Cited

U.S. PATENT DOCUMENTS

| 3,302,648 | A | | 2/1967 | Nelson et al. |
| 5,673,955 | A | * | 10/1997 | Neubauer ................ 294/31.1 |
| 5,697,949 | A | | 12/1997 | Giurtino et al. |
| 2004/0186513 | A1 | | 9/2004 | Dworschak et al. |

FOREIGN PATENT DOCUMENTS

| DE | 43 39 992 | 3/1995 |
| DE | 201 13 020 | 11/2001 |
| DE | 201 13 017 | 12/2001 |
| DE | 101 38 394 | 2/2003 |
| DE | 101 38 392 | 3/2003 |
| EP | 0 444 372 | 9/1991 |
| WO | 97/07726 | 3/1997 |

* cited by examiner

*Primary Examiner*—Lee S. Cohen  
(74) *Attorney, Agent, or Firm*—Lipsitz & McAllister, LLC

(57) ABSTRACT

A two-part medical instrument is proposed, comprising a first part having a peg and a second part having a peg receiver, wherein first part and second part are connected to one another by a peg/peg receiver connection and the first part is made of a plastics material, wherein the peg has a peripheral edge bead.

21 Claims, 2 Drawing Sheets

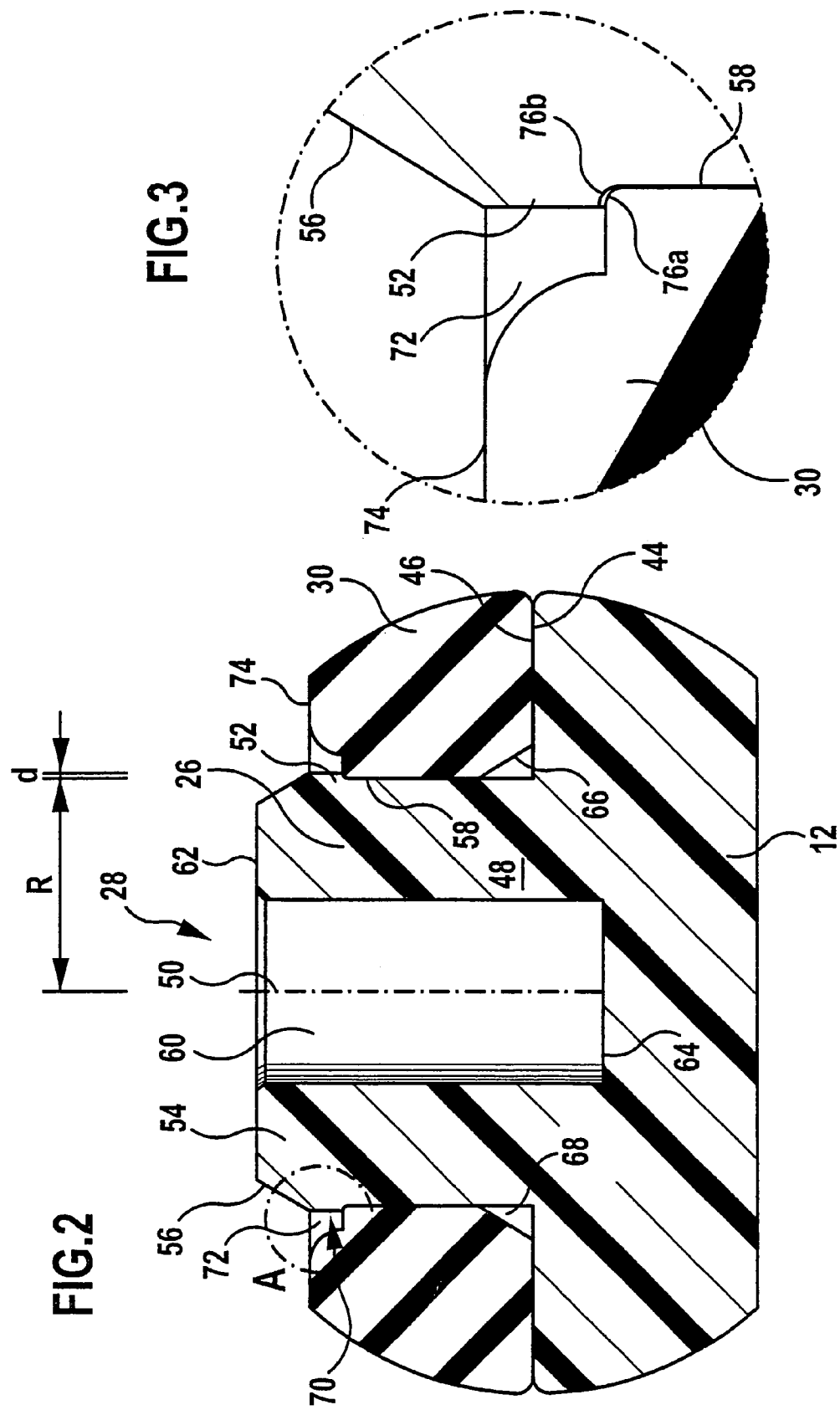

TWO-PART MEDICAL INSTRUMENT

This application is a continuation of international application No. PCT/EP2003/009433 filed on Aug. 26, 2003.

The present disclosure relates to the subject matter disclosed in international application No. PCT/EP2003/009433 of Aug. 26, 2003 and German application No. 102 42 152.8 of Sep. 5, 2002, which are incorporated herein by reference in their entirety and for all purposes.

BACKGROUND OF THE INVENTION

The invention relates to a two-part medical instrument, comprising a first part having a peg and a second part having a peg receiver, wherein first part and second part are connected to one another by a peg/peg receiver connection and the first part is made of a plastics material.

From U.S. Pat. No. 3,302,648 a clamping implement is known, which comprises two handle levers, wherein seated integrally on one handle lever is a peg stud of a quartered or three-prong segmental structure. Seated on the peg stud is a head, which is subdivided in segments in continuation of the peg stud segments.

SUMMARY OF THE INVENTION

In accordance with the invention, a two-part medical instrument is provided which is easy to manufacture.

In accordance with the invention, the peg has a surrounding edge bead.

A peripheral edge bead on the peg is easy to manufacture integrally with the peg without, for example, having to provide separate segments. Particularly in the case of medical instruments where no or only low transverse forces occur, such as grasping instruments, it is therefore possible to achieve easy and inexpensive manufacture.

As no segments have to be provided, the peg having the peripheral edge bead is consequently also more stable, so that the risk of a segment breaking off does not exist. This is particularly important for a medical instrument because, if, for example, too high a force is exerted, it is necessary to prevent parts of the instrument from breaking off as these may, for example, fall into a wound or the functionality of the instrument is impaired during a treatment procedure on the human body.

In particular, it is therefore possible for the first part having the peg to be manufactured in a simple manner by a moulding method.

In particular, the edge bead is received by a bead receiver, so that the peg does not project or projects only slightly beyond the second part.

By virtue of the edge bead being seated in the bead receiver it is possible to minimize the contact surface between edge bead and bead receiver, i.e. the contact surface between peg and peg receiver, so that in particular an ability of the two parts to pivot relative to one another is not prevented or substantially impeded. It is then possible to manufacture medical instruments, such as e.g. clamps and scissors, in which the ability of the two parts to pivot relative to one another starting from a closed position is not substantially impeded.

Advantageously, the peg receiver has a larger diameter in the region of the bead receiver than outside of the bead receiver. This allows the provision of a contact surface, by means of which a movement of the second part away from the first part is preventable.

It is advantageous when the height of the bead receiver is smaller than the height of the peg receiver outside of the bead receiver. This allows easy manufacture of the edge bead because it is then only a very small component on the peg.

In particular, in said case the bead receiver is disposed on a surface of the second part, thereby minimizing the outlay for forming the bead receiver because the bead receiver may, for example, be introduced by milling from the surface or, given a suitable mould construction, be manufactured by means of a moulding method.

In particular, it is provided that the bead receiver is disposed in a countersunk manner. In this way, it is also possible to achieve the effect that the peg projects by a minimized amount beyond the second part.

It is further advantageous when the bead receiver has an annular cross section around the peg receiver. It is thereby possible to guarantee that the peg is rotatable in the peg receiver, wherein a minimized contact surface is provided, which is sufficient to prevent movement of the second part away from the first part but not the pivoting movement of the two parts relative to one another.

The peg may take the form of a solid peg or have a central recess. By said means, an elastic compression of the peg transversely of its longitudinal direction may be achieved, which facilitates the introduction of the peg into the peg receiver. It is therefore possible through elastic compression transversely of the longitudinal direction for the introduction to be facilitated, whilst removal of the edge bead from the bead receiver entails the overcoming of a much higher force with a direction substantially parallel to the longitudinal direction (in a direction parallel to the normal of the contact surfaces).

The central recess is advantageously of a cylindrical construction in order thereby to obtain a rotationally symmetrical construction.

The central recess advantageously has a larger height than the peg, i.e. the central recess extends below the surface of the first part that faces the second part. By said means, a greater elastic transverse mobility of peg walls may be achieved in order thereby likewise to facilitate the introduction of the peg into the peg receiver.

The solution according to the invention makes it possible in principle to design the second part with a lower elasticity. It is however advantageous when the second part is made likewise of a plastics material, and in particular is made of the same material as the first plastics material in order thereby to obtain compatible properties of the two parts.

The pivot is advantageously of a rotationally symmetrical construction in order thereby to obtain, for example, a good ability of the two parts to pivot relative to one another.

For the same reason, it is advantageous when the peg receiver is of a rotationally symmetrical construction.

The first part having the peg integrally formed thereon may be manufactured easily when the peg has a continuous cylindrical surface. Continuous, in this case, refers to directions at right angles to the radial direction. The peg is therefore not divided into segments, thereby making the peg easier to manufacture and preventing the breaking-off of individual segments.

It is quite particularly advantageous when the peg receiver has an insertion recess for the peg that faces the first part. In order to assemble the two parts, the edge bead may therefore be introduced into this insertion recess and the peg may then be pressed upwards in order in said manner finally to bring the edge bead into its bead receiver.

It is then likewise advantageous when the peg at its upper end is of a bevelled construction. Thus, when the peg is pressed in its longitudinal direction into the peg receiver, transverse forces are then exerted particularly in interaction with the insertion recess and press the peg walls having the edge bead in the direction of the axis of the peg. This then allows the edge bead to be conveyed through the part of the peg receiver that is situated outside of the bead receiver.

The peg having the edge bead is advantageously so dimensioned and designed in relation to the peg receiver that the peg owing to its elasticity is pushable into the peg receiver and, in particular, the edge bead is bringable into the bead receiver and/or placeable onto a surface of the second part. In this manner, a detachable or non-detachable connection may therefore be established between the peg and the peg receiver, wherein it is also still possible for the two parts to pivot relative to one another. It is therefore possible to establish a secure connection, whilst the two individual parts themselves are easy to manufacture. To produce the fastening, only relatively low assembly forces have to be exerted.

In particular, in said case the peg is designed in such a way that it is rotatable in the peg receiver. It is then possible to manufacture e.g. two-part medical clamps or other holding instruments.

It is further advantageous when the edge bead is so designed that first part and second part are fastened to one another, i.e. the movement of the second part away from the first part is prevented, by means of said edge bead.

In particular, it is provided that the peg is designed in such a way that transversely of a height direction it has an elastic extensibility of between 1% and 5%. It is thereby ensured, on the one hand, that a large enough contact surface is provided by the contact between edge bead and bead receiver to fasten the two parts to one another and, on the other hand, it is ensured that the peg is bringable into the peg receiver.

It is further advantageous when the edge bead projects in particular transversely of a peg longitudinal direction by a width of 1% to 5% beyond the peg region that is seated in the peg receiver outside of the edge bead. By said means, it is possible to realize the effect whereby the connection between peg and peg receiver is easy to establish, wherein a secure fastening of the two parts is achieved.

The following description of a preferred form of construction is used in conjunction with the drawings to explain the invention in detail.

BRIEF DESCRIPTION OF THE DRAWINGS

FIG. 2 a sectional side view of a connection in accordance with the invention between peg and peg receiver and FIG. 3 an enlarged view of the region A according to FIG. 2.

DETAILED DESCRIPTION OF THE INVENTION

Figure 1:
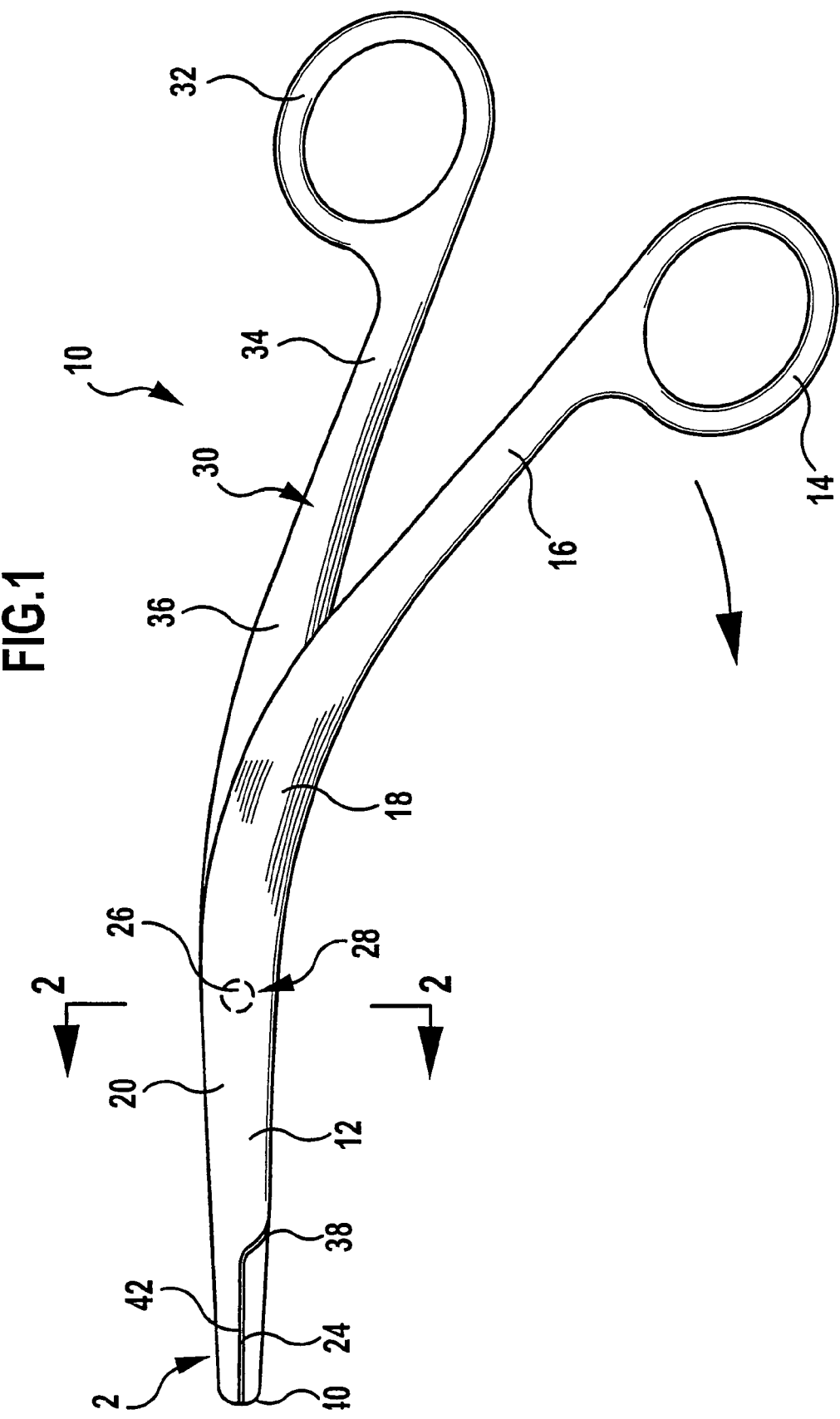
FIG. 1 a plan view of an embodiment of a medical instrument in accordance with the invention.

An embodiment of a two-part medical instrument according to the invention is, for example, a clamp in the form of a grasping instrument, which is illustrated in FIG. 1 and denoted as a whole by 10. This clamp comprises a first part 12 (male part), which is manufactured from a plastics material such as PEEK. In the illustrated embodiment, the first part 12 has a ring handle 14, which is seated on a handle ear region 16. This handle ear region 16 is adjoined by a curved middle region 18, which runs into an end region 20. The end region 20 has a working end 22, on which e.g. gripping surfaces 24 are formed or a cutting edge is disposed.

Seated in the middle region 18 is a peg 26 (pin or stud) for forming a peg/peg receiver connection 28, by means of which the first part 12 is connected journably to a second part 30 (female part).

The second part 30 likewise has a ring handle 32, which is seated on a handle ear region 34, which runs into a curved middle region 36. In the illustrated embodiment, the middle region 36 of the second part 30 is curved to a lesser extent than the middle region 18 of the first part 12, so that in the closed state of the clamp the two ring handles 32 and 14 are spaced apart from one another.

The middle region 36 of the second part 30 runs into an end region 38, which has a working end 40 e.g. with gripping surfaces 42 that face the gripping surfaces 24 of the first part 12, thereby enabling an article to be gripped between them.

The end regions 20 and 38 of the first part 12 and the second part 30 are in said case designed and tuned to one another in such a way that the two parts 12 and 30 are prevented from being journabled towards one another upon attainment of the closed position, in which, for example, the gripping surfaces 24 and 42 are at least partially in mutual abutment.

Starting from this closed position, the first part 12 may be swivelled away from the second part 30 in such a way that the distance between the gripping surfaces 24 and 42 increases, i.e. a gap opens up. By journabling the first part 12 towards the second part 30 and exerting a force, an article may be clamped between the gripping surfaces 24 and 42, wherein boosted in particular by the curved construction of the first part 12 a corresponding leverage may be exerted upon the article.

The first part 12 has a flat surface 44 facing the second part 30. The second part 30 likewise has a flat surface 46 facing the first part 12. The peg 26 projects from this flat surface 44 of the first part 12, wherein the peg 26 is integrally connected to the first part 12.

The peg 26 comprises a first cylindrical region 48, which has an outer surface that corresponds to a convex surface of a cylinder and that is rotationally symmetrical relative to a longitudinal axis 50 of the peg 26. In the first cylindrical region 48 the peg 26 has a substantially smooth surface without interruptions, recesses or the like.

The first cylindrical region 48 is adjoined by an edge bead 52, which runs round in the manner of a ring, wherein in the region of the edge bead 52 the peg 26 has a larger diameter than at the first cylindrical region 48. The edge bead 52 in said case projects transversely of the longitudinal axis 50 beyond the first cylindrical region 48 by a radial width d, which lies in the region of between ca. 1% to 5% of the radius R of the peg 26 in the first cylindrical region 48. The transitions between the regions and edges are preferably rounded off.

The height of the first cylindrical region 48 parallel to the longitudinal axis 50 is much greater than the height of the edge bead 52 in this direction.

The edge bead 52 is adjoined in the direction of the longitudinal axis 50 by a chamfered region 54, which is in the shape of a truncated cone. It therefore has a bevelled surface 56, which runs round in the shape of a ring and which, as is explained in more detail below, is used to facilitate the introduction of the peg 26 into a peg receiver 58 of the second part 30.

The peg 26 has a central recess 60, which is of a cylindrical construction and in particular is concentric around the longitudinal axis 50 of the peg 26. The height of this central recess 60, measured from a top end 62 of the peg 26, is in said case such that the central recess 60 extends beyond the surface 44 of the first part 12, i.e. a bottom end 64 of the central recess 60 that is remote from the top end 62 of the peg 26 and forms the base of the central recess 60 lies below the surface 44 of the first part 12.

The peg 26 is so dimensioned and so designed that in interaction with the central recess 60 an elastic compressibility transversely of the longitudinal axis 50 in the region of between 1% and 5% is achievable in order to allow the peg 26 to be introducible into the peg receiver 58 and in order by means of the edge bead 52 to establish a peg/peg receiver connection, by means of which the first part 12 and the second part 30 are held on one another rotatably with an axis of rotation that coincides with the longitudinal axis 50.

In particular, the first part 12 is manufactured from such a material and in particular plastics material that has an elastic elongation in the region of between ca. 1% and 5%.

The peg receiver 58 formed in the second part 30 is used to receive the peg 26. The peg receiver 58 is formed in the second part 30 by a cylindrical opening, which extends coaxially with the longitudinal axis 50.

The second part 30 is bevelled at the side of the peg receiver 58 facing the first part 12 and has a peripheral sloping surface 66. The sloping surface 66, which is a lateral surface of a truncated cone, is in said case matched to the bevelled surface 56 of the peg 26 in such a way that the introduction of the peg 26 into the second part 30 from the direction of the surface 46 is facilitated; the sloping surface 66 therefore forms on the peg receiver 58 an insertion recess 68 for the peg 26.

The peg receiver 58 further comprises a bead receiver 70 for receiving the edge bead 52 of the peg 26. This bead receiver 70 takes the form of an, in cross section, annular recess 72 in a surface 74 of the second part 30, wherein this surface 74 lies remote from the other surface 46.

The bead receiver 70 has, in the direction of the longitudinal axis 50, a smaller height than the remaining peg receiver 58 outside of the bead receiver 70. The bead receiver 70 is set back relative to the surface 74, i.e. is countersunk relative thereto, so that the edge bead 52 is inserted in the bead receiver 70 so as to lie at least partially below the surface 74. Transitions and edges of the bead receiver 70 are preferably rounded off.

In a preferred variant of a form of construction, which is shown in FIG. 2, the edge bead extends flush with the surface 74 of the second part 30, so that only the region 54 of the peg 26, not however the edge bead 52, projects beyond the second part 30.

Formed on the edge bead 52 and the bead receiver 70 there are in each case annular contact surfaces 76a and 76b, by means of which the movement of the second part 30 away from the first part 12 is prevented. The movement of the second part 30 towards the first part 12 is prevented by contact of the surfaces 44 and 46. The contact surfaces 76a, 76b are in said case so dimensioned that for movement of the second part 30 away from the first part 12 the elastic force of the peg 26 at the edge bead 52 substantially parallel to the longitudinal axis 50 has to be overcome. This elastic force that has to be overcome is in said case considerably higher than the elastic transverse force that has to be overcome when the peg 26 is introduced into the peg receiver 58.

In particular, in the region of the contact surface 76b of the peg receiver 58 there is an, in cross section, step-shaped transition, i.e. the contact surface 76b lies substantially at right angles to a hollow-cylindrical lateral surface of the peg receiver 58 in the region, in which the first cylindrical region 48 of the peg 26 is received by the peg receiver 58.

The second part 30 may be manufactured likewise from a plastics material. In particular, it is manufactured from the same material as the first part 12.

The two parts 12 and 30 are manufactured separately, wherein they are in each case integral parts. (Working tools such as cutting edges may be formed separately.) In said case, the peg 26 is formed in the first part 12 and the peg receiver 58 is formed in the second part.

The peg 26 is pushed through the insertion recess 68 into the peg receiver 58 (or, conversely, the peg receiver 58 is pushed onto the peg 26).

Owing to the elastic properties of the material of the first part 12 and the central recess 60, the edge bead 52 may then be displaced in the peg receiver 58 in the direction of the longitudinal axis 50 until the bead receiver 70 is reached and, there, the edge bead 52 springs back transversely of the longitudinal axis 50 and is therefore received by the bead receiver 70. Consequently, the second part 30 is then fastened rotatably to the first part 12, wherein the individual parts 12 and 30 may be assembled using low assembly forces. This assembly may be carried out by hand or by machine.

By suitably selecting as a material in particular for the first part 12 having the peg 26 a plastics material that has an elastic elongation in the region of between ca. 1% to 5%, it is therefore possible to establish a secure connection in the form of a peg interlock between the two parts 12 and 30.

Given a corresponding dimension of the edge bead 52, which runs round without interruptions, a detachable or a non-detachable peg interlock may be established.

The invention claimed is:

1. Two-part medical instrument, comprising:
    a first part having an integral peg; and
    a second part having a peg receiver;
    wherein:
        the first part and the second part are connected to one another by a peg/peg receiver connection;
        the first part is made of a plastics material;
        the peg has a one-piece peg body with a continuous cylindrical surface and a continuous surrounding edge bead;
        said edge bead has a larger diameter than the peg body for securing the peg in the peg receiver and forming the peg/peg receiver connection;
        said peg receiver has a first opening that receives the peg body and a second opening that receives the edge bead;
        said edge bead having a larger diameter than the first opening;
        said second opening having a larger diameter than the first opening;
        said second opening having a contact surface which prevents the movement of the second part and the first part away from each other by contact with the edge bead; and
        the peg with the peg body and edge bead is elastic and pushable through the first opening into said peg receiver.

2. Two-part medical instrument according to claim 1, wherein a height of the second opening in a longitudinal direction of the peg receiver is smaller than a height of the first opening.

3. Two-part medical instrument according to claim 1 wherein the second opening is disposed at a surface of the second part.

4. Two-part medical instrument according to claim 3, wherein the second opening is disposed in a countersunk manner.

5. Two-part medical instrument according to claim 1, wherein the second opening has an annular cross section around the peg receiver.

6. Two-part medical instrument according to claim 1, wherein the peg has a central recess.

7. Two-part medical instrument according to claim 6, wherein the central recess is of a cylindrical shape.

8. Two-part medical instrument according to claim 6, wherein the central recess has a greater height than the peg.

9. Two-part medical instrument according to claim 6, wherein the central recess extends below a surface of the first part.

10. Two-part medical instrument according to claim 1, wherein the second part is made of a plastics material.

11. Two-part medical instrument according to claim 1, wherein the peg receiver is of a rotationally symmetrical shape.

12. Two-part medical instrument according to claim 1, wherein the peg receiver has an insertion recess for the peg that faces the first part.

13. Two-part medical instrument according to claim 1, wherein the peg is bevelled at its top end.

14. Two-part medical instrument according to claim 1, wherein the peg body and the edge bead are adapted so that the peg is insertable with the edge bead into second opening.

15. Two-part medical instrument according to claim 1, wherein the peg is adapted to be rotatable in the peg receiver.

16. Two-part medical instrument according to claim 1, wherein the edge bead is adapted so that the first part and the second part are detachably fastened to one another by said edge bead.

17. Two-part medical instrument according to claim 1, wherein the peg is adapted so that it has an elastic extensibility of between 1% and 5% transversely of a height direction.

18. Two-part medical instrument according to claim 1, wherein the edge bead projects in one direction by a width of 1% to 5% beyond the peg body.

19. Two-part medical instrument according to claim 1, wherein the edge bead projects transversely of a longitudinal direction of the peg beyond the peg body.

20. Two-part medical instrument, comprising:
a first part having an integral peg; and
a second part having a peg receiver;
wherein:
the first part and the second part are connected to one another by a peg/peg receiver connection;
the first part is made of a plastics material;
the peg has a one-piece peg body with a continuous cylindrical surface and a continuous surrounding edge bead;
said edge bead has a larger diameter than the peg body for securing the peg in the peg receiver and forming the peg/peg receiver connection;
said peg has a central recess which extends to a top end of the peg and through the edge bead arranged at said top end of said peg; and
the peg with the peg body and edge bead is elastic and pushable into said peg receiver.

21. Two-part medical instrument, comprising:
a first part having a peg; and
a second part having a peg receiver;
wherein:
the first part and the second part are connected to one another by a peg/peg receiver connection;
the first part is made of a plastics material;
the peg has a peg body and a surrounding edge bead;
the peg has a central recess which has a greater height than the peg;
said edge bead has a larger diameter than the peg body for securing the peg in the peg receiver and forming the peg/peg receiver connection;
said peg receiver has a first opening that receives the peg body and a second opening that receives the edge bead;
said edge bead having a larger diameter than the first opening;
said second opening having a larger diameter than the first opening;
said second opening having a contact surface which prevents the movement of the second part and the first part away from each other by contact with the edge bead; and
the peg with the peg body and edge bead is elastic and pushable into said peg receiver.

* * * * *